(12) United States Patent
Graichen et al.

(10) Patent No.: US 10,060,843 B2
(45) Date of Patent: Aug. 28, 2018

(54) DEVICE AND A METHOD FOR MEASURING FLUID-MECHANICALLY EFFECTIVE MATERIAL PARAMETERS OF A FLUID

(71) Applicant: Berlin Heart GmbH, Berlin (DE)

(72) Inventors: Kurt Graichen, Berlin (DE); Andreas Arndt, Berlin (DE); Peter Nuesser, Kleinmachnow (DE)

(73) Assignee: Berlin Heart GmbH, Berlin (DE)

( * ) Notice: Subject to any disclaimer, the term of this patent is extended or adjusted under 35 U.S.C. 154(b) by 118 days.

(21) Appl. No.: 15/046,507

(22) Filed: Feb. 18, 2016

(65) Prior Publication Data

US 2016/0193398 A1 Jul. 7, 2016

Related U.S. Application Data

(63) Continuation of application No. 13/512,426, filed as application No. PCT/EP2010/007442 on Nov. 30, 2010, now Pat. No. 9,297,735.

(60) Provisional application No. 61/265,007, filed on Nov. 30, 2009.

(30) Foreign Application Priority Data

Nov. 30, 2009 (EP) .................................... 09075526

(51) Int. Cl.
| | | |
|---|---|---|
| *G01N 11/16* | (2006.01) | |
| *A61M 1/10* | (2006.01) | |
| *A61M 1/12* | (2006.01) | |

(52) U.S. Cl.
CPC ........... *G01N 11/16* (2013.01); *A61M 1/1015* (2014.02); *A61M 1/101* (2013.01); *A61M 1/1031* (2014.02); *A61M 1/1086* (2013.01); *A61M 1/122* (2014.02); *A61M 2205/3334* (2013.01); *G01N 11/162* (2013.01)

(58) Field of Classification Search
CPC .... A61M 1/1015; G01N 11/16; G01N 11/162
USPC ................................................ 73/54.23–54.35
See application file for complete search history.

(56) References Cited

U.S. PATENT DOCUMENTS

| | | | |
|---|---|---|---|
| 3,976,339 A | * | 8/1976 | Sabnis ............... B60G 17/0157 310/90.5 |
| 4,683,391 A | | 7/1987 | Higuchi |
| 4,688,998 A | | 8/1987 | Olsen et al. |
| 4,779,614 A | | 10/1988 | Moise |
| 5,720,721 A | | 2/1998 | Dumas et al. |
| 5,725,357 A | | 3/1998 | Nakazeki et al. |

(Continued)

FOREIGN PATENT DOCUMENTS

| | | |
|---|---|---|
| CN | 101282748 A | 10/2008 |
| DE | 196 13 388 A1 | 10/1996 |

(Continued)

*Primary Examiner* — Peter Macchiarolo
*Assistant Examiner* — Nathaniel Kolb
(74) *Attorney, Agent, or Firm* — Brinks Gilson & Lione

(57) ABSTRACT

A method and a device for the measurement of fluid-mechanically effective parameters of a fluid, with a fluid pump which comprises a delivery element (2) which is mounted in a magnet bearing (10, 10a, 11, 11a), according to the invention, envisages the delivery element (2) of the fluid pump being excited into an oscillation by way of an excitation device (16, 44), wherein the oscillation parameters as well as, as the case may be, the oscillation behavior is measured, and parameters of the fluid are determined from this.

10 Claims, 3 Drawing Sheets

(56) References Cited

U.S. PATENT DOCUMENTS

| | | | |
|---|---|---|---|
| 5,798,454 A | 8/1998 | Nakazeki et al. | |
| 6,527,699 B1 | 3/2003 | Goldowsky | |
| 6,711,943 B1 | 3/2004 | Schöb | |
| 7,578,782 B2 * | 8/2009 | Miles | A61M 1/101 415/900 |
| 2005/0214131 A1 * | 9/2005 | Miles | A61M 1/101 417/44.11 |
| 2008/0091265 A1 * | 4/2008 | Nuesser | F04D 3/02 623/3.13 |
| 2008/0262289 A1 | 10/2008 | Goldowsky | |

FOREIGN PATENT DOCUMENTS

EP       0 967 475 A1    12/1999
EP       0 971 212 A1    1/2000

\* cited by examiner

DEVICE AND A METHOD FOR MEASURING FLUID-MECHANICALLY EFFECTIVE MATERIAL PARAMETERS OF A FLUID

CROSS-REFERENCE TO RELATED APPLICATIONS

This application is a continuation application of, and claims priority under 35 USC § 120 to, U.S. patent application Ser. No. 13/512,426, filed May 29, 2012, entitled "DEVICE AND A METHOD FOR MEASURING FLUID-MECHANICALLY EFFECTIVE MATERIAL PARAMETERS OF A FLUID", which is a 371 nationalization of PCT/EP2010/007442, filed Nov. 30, 2010, which in turn claims benefit of U.S. Provisional Application 61/265,007 filed Nov. 30, 2009, and European patent application 09075526.5 filed Nov. 30, 2009.

BACKGROUND

The invention lies in the field of fluid mechanics and in particular of fluidic measurement of material characteristics of fluids.

On the one hand, the knowledge of flow resistances in channels through which fluid flows and on the other hand, likewise the exact knowledge of the material characteristics of the flowing fluid, thus for example of the liquid or of the gas, which is delivered through the channels, are important for the assessment and design of fluid-mechanical devices. The respective characteristics are basically intrinsic of the material, but individually also dependent on the different constraints such as the temperature or also the flow speed for example (for example with non-Newtonian fluids).

It is particularly with applications in medical technology, when biologically effective fluids and ones, which are subjected to biological processes, are to be delivered, that the respective characteristics of these fluids may continuously change. A particular application of this type is the delivery of the body's own blood which, with regard to its viscosity, is dependent on different physiological processes. Accordingly for example, a pump power, with a pump which is applied for delivering blood, may be adapted to a continuously monitored blood viscosity.

Different methods for measuring the density and/or the viscosity of fluids are known from the state of the art.

Suitable viscometers are for example known from the literature as flow cups, falling body viscometers, measurement agitation drives, and also from the standardisation.

Likewise known are viscosity and density measurement apparatus, which measure the effect of a fluid on an oscillating element which is located in this.

Moreover, a measuring method is known from the US patent document 6581476 B1, with which the rotor of a synchronous motor is driven within a fluid and simultaneously the rotational speed and energy consumption are measured for determining the viscosity.

Against the background of the state of the art, it is the object of the present invention to provide a method and a device, by way of which one may measure fluid-mechanical characteristics of a fluid with as little as possible effort, but in a reliable and accurate manner.

SUMMARY

According to the invention, thereby, a fluid pump is used, which comprises a delivery element mounted in a magnet bearing. Moreover, the device for measuring the material parameters comprises an excitation device for oscillation excitation of the delivery element against a counter-force produced by the magnet bearing, as well as a sensor device for measuring the oscillation behaviour of the delivery element.

The device according to the invention therefore, with the application of a fluid pump which is usually present in any case for the delivery of the fluid, permits the measurement of the fluid-mechanically effective material parameters of interest, without a special element having to be fitted into the flow path, or samples having to be removed in a complicated manner. Only an excitation device for the delivery element and a sensor device for detecting the oscillation behaviour are necessary. Thereby, a typical delivery element is formed by a rotor, which, depending on the construction type of the pump, delivers fluid in the axial or radial direction and may be suitably mounted in a magnet bearing in a low-friction manner. Such a magnet bearing may accordingly be designed as a radial bearing or thrust bearing. An active closed-loop control of the bearing is envisaged, in order to stabilise the position of the delivery element and to compensate reactions of the fluid to be delivered on the bearing, on application of the pump power. Such a magnet bearing closed-loop control usually envisages a position sensor for the delivery element, as well as a control device for controlling additionally produced magnetic forces, for example by way of an electromagnet. The control device may be used for example to control the current through a coil producing a magnetic field. The respective position sensor may likewise carry out the measurement of the position of the delivery element by way of a sensitive magnet coil.

If an active bearing closed-loop control in the direction of the magnet bearing in which the oscillation also takes pace is envisaged, one must ensure that the closed-loop control does not interact with the oscillation in an uncontrolled manner. This for example may be effected by way of the closed-loop control having a different time constant than the oscillation, for example operating at a significantly higher-frequency manner or with a much lower frequency than the oscillation.

Also, for the exciting of the delivering element and for sensing its movement in response to the excitation, a separate actor and sensor different from the sensors and actors of the closed loop control can be used in order to avoid interferences of the viscosity measurement and the function of the closed-loop control of the magnetic bearing. In one embodiment, the exciting element independent of the closed loop control or, in another embodiment, the sensor can be part of the closed loop control of the bearing and the actor can be a separate one.

The actors and sensors for the viscosity measurement, e.g. for the measurement of the oscillation properties of the delivering element can act in axial or radial direction of a rotor representing a delivery element or they can refer to and sense a tilting movement of the rotor.

One may also envisage the bearing closed-loop control interacting with the oscillation, wherein then the changing bearing forces must be taken into account with the evaluation of the oscillation.

The device according to the invention for analysis of the oscillation in the sensor device advantageously comprises a first sensor for measuring an oscillation frequency of the delivery element and/or a second sensor for measuring the oscillation amplitude of the delivery element as well as, as the case may be, a time detection device for measuring the oscillation build-up and/or oscillation decay behaviour of the delivery element.

Therefore, the measurement of the oscillation properties of the delivering element can preferably take place in the time domain, where the answer of the system is measured with consideration of the point of time of the beginning or the end of the exciting process. For example, the excitation may be an impulse or a limited number of impulses or a single rectangular signal and the answer of the system can be thereafter. This has the advantage, that the detected signals are not disturbed by the exciting signal. Also, it can be an advantage if only a frequency or a damping time and not an absolute value of an amplitude of an oscillation has to be measured.

The excitation signal may also be periodical, wherein the development of the system oscillation from the beginning until reaching a stable status can be detected.

The natural frequency after completion of the excitation, as well as the oscillation amplitude or oscillation build-up and/or oscillation decay behaviour of the free oscillator have a substantial dependency on the density and/or the viscosity of the fluid which surrounds the delivery element. Moreover, with the measurement of these variables, the geometric conditions within the fluid pump play a part, if for example the fluid is periodically displaced in gaps by way of the oscillation. Thus a calibration is necessary for determining the fluid-mechanical characteristics of the fluid by way of the described measurement.

The physically relevant relationship between the searched, fluid-mechanically effective material parameters (substance values)

ρ density of the fluid in kg/m$^3$

η dynamic viscosity of the fluid in Pas and the variables which are detectable with regard to measurement technology on oscillation of the magnetically mounted rotor after a suitable oscillation excitation, may be described in a simplified in the following way: A movement equation of the form $$m_{total} * \frac{d^2x}{dt^2} + C_V * \frac{dx}{dt} + k*x = 0$$

applies to the rotor oscillating in the direction of the rotation axis of the rotor, the x-axis, with $m_{total}$ the total mass, $C_V$ the friction coefficient, and k the stiffness of the bearing in the x-direction.

It is known that on oscillation of a body in a fluid surrounding it, not only the body itself, but also a certain share of the adjacent fluid must be accelerated. The total mass $m_{total}$ thus not only includes the known motor mass but also an "additional mass", whose size depends on the geometry of the arrangement and the density of the surrounding fluid. The size of the "geometry factor" of this "additional mass" is known for many arrangements.

The force equilibrium which is described in the above oscillation equation is furthermore determined by way of speed-proportional friction forces. The factor $C_V$ is proportional to the searched dynamic viscosity of the fluid.

Accordingly, the searched material characteristics (substance values) of density and dynamic viscosity are hidden in the oscillation equation and may be determined by way of an analysis of the oscillation behaviour of the rotor on the basis of suitable calibrations.

Basically, with the device according to the invention, one may envisage the excitation device being connected to a device for the closed-loop control of a magnetic bearing force.

With this for example, by way of applying a current to a magnet coil, not only is the magnetic bearing force closed-loop controlled, but also a thrust impulse onto a delivery element for exciting an oscillation is given.

Also, the first and/or second sensor may be connected to a position sensor of the magnet mounting of the delivery element, thus for example to a sensory magnet coil, constructively unified with this or narrowed or even be identical to it.

With this method, an oscillation is applied onto a delivery element of a fluid pump by way of an excitation device, and this delivery element is mounted in a magnet bearing, and the oscillation behaviour of the delivery element is measured.

Advantageously thereby, the oscillation frequency of the delivery element, its amplitude or a decay time of the oscillation or also the energy expense with the oscillation excitation, are measured.

This may be carried out in a particularly accurate manner with an idle delivery element. However, it may also be advantageous to carry out the measurement during the fluid delivery, in order to avoid interruptions of the fluid delivery and despite this, to be able to continuously monitor the material characteristics. This is particularly advantageous with the delivery of biologically effective fluid, in particular in living bodies, in order not to disturb the respective processes which are dependent on the supply with the fluid. Finally, the invention also relates to the use of a fluid pump for carrying out the measurement method of the described type.

The invention is shown and hereinafter described by way of one embodiment example in a drawing.

BRIEF DESCRIPTION OF THE DRAWINGS

Thereby, there are shown in.

DESCRIPTION OF A PREFERRED EMBODIMENT

Figure 1:
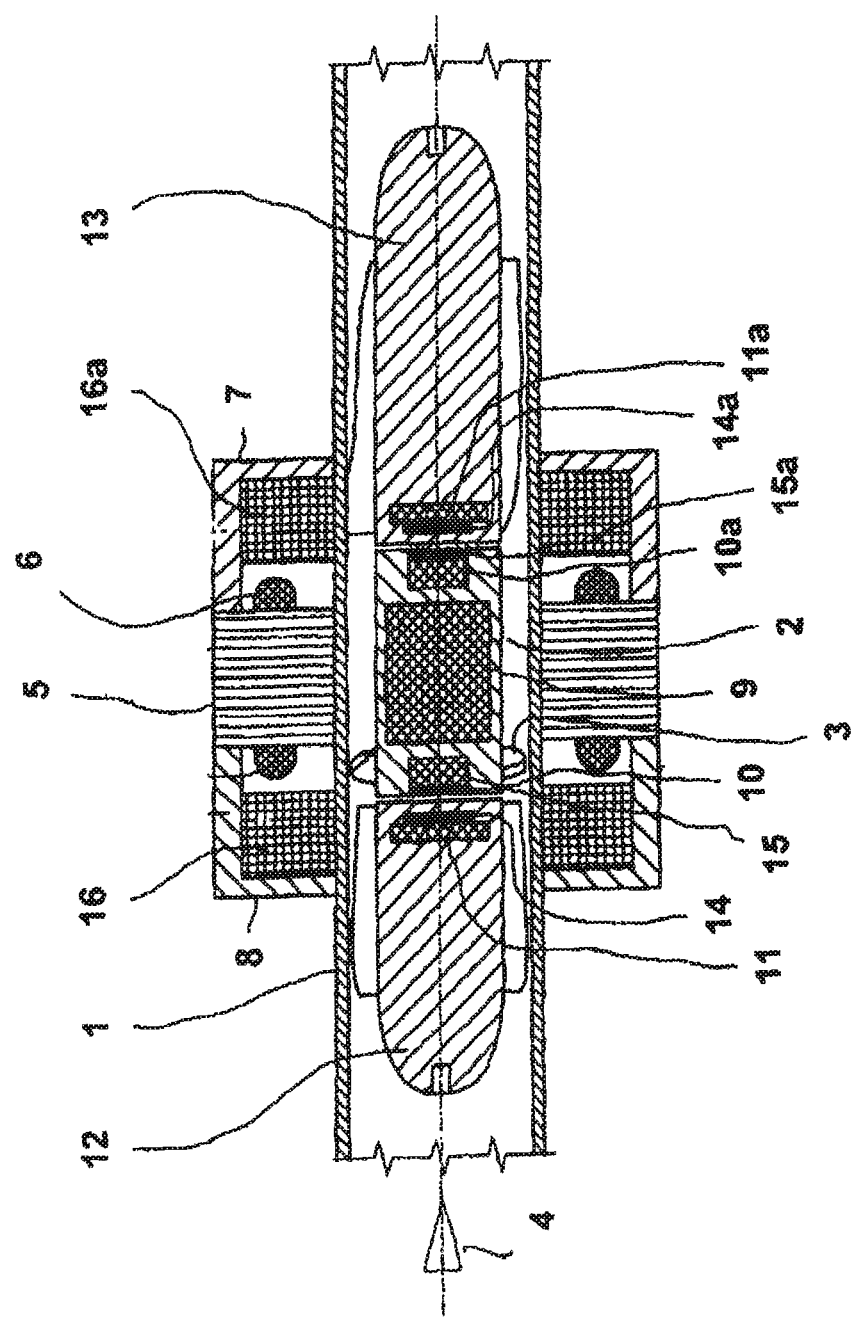
FIG. 1 in a longitudinal section, schematically, an axial pump with a closed-loop controlled, magnetic thrust bearing, FIG. 2 schematically, the manner of functioning of the magnetic bearing closed-loop control and of the pump drive, FIG. 3 schematically, the measurement of the reaction force on the thrust bearing of the pump in delivery operation, the measurement of the rotational speed and, resulting from this with the known fluid characteristics, the deduction of fluid-mechanical characteristics of a component through which fluid flows and which is different to the pump, as well as FIG. 4 schematically, the function of the oscillation excitation with an axial pump, and the measurement of the oscillation and FIG. 5 a measurement diagram of the oscillation behaviour.

FIG. 1 schematically shows a magnet-mounted axial pump in a longitudinal section, as is applied for example as a blood pump for the human body. The pump is inserted into a cylindrical tube 1 and comprises a rotor 2 with rotor blades 3 for advancing a fluid in the flow direction 4.

The drive for the rotor 2 envisages a lamination bundle 5, windings 6, as well as yoke parts 7, 8 which together with the lamination bundle 5, form a highly permeable magnet circuit which is closed via permanent magnets 9 in the core of the rotor 5, so that as a whole a synchronous motor or also a brushless d.c. motor with an outer-lying stator is formed, which is electronically commutated.

The rotor 2 is mounted in a magnetically contact-free manner in the axial direction by way of permanent magnets 10, 10*a* whose magnet axis is aligned parallel to the flow direction 4, as well as by way of stationary permanent magnets 11, 11*a*.

The permanent magnets 10, 11 and 10*a*, 11*a* are in each case aligned such that they attract in pairs in the axial direction. With this, at best a weak equilibrium is formed in the axial direction 4, so that additionally, one must provide a closed-loop control device for contact-free mounting.

For detecting the axial position of the rotor 2, in each case a sensor coil 14, 14*a* is provided in the stationary part of the axial pump 12, 13, said stationary part lying in the extension of the rotor 2 within the tube 1, opposite which sensor coil, within the rotor, in each case a short circuit ring 15*a*, 15*a* lies, so that in each case the distance to the respective short circuit ring 15, 15*a* and thus the axial position of the rotor 2 may be measured by way of the inductance of the sensor coils 14, 14*a*.

The respective measurement variables are fed as output variables to a control device which controls a current through two control coils 16, 16*a*, in dependence on the measured position or on the difference to the desired position, of the rotor, said coils strengthening or weakening the respective axial fields of the permanent magnets 11, 11*a*, in order to control the attraction force of the permanent magnets 10, 11, 10*a*, 11*a* in a manner such that the rotor 5 assumes a desired position in the axial direction.

If now the rotor 2, by way of switching on the drive, is set into rotation in a manner such that a fluid located in the tube 1 is delivered in the direction 4, then a reaction force results, which is opposite to the force acting on the fluid in the direction 4 and which temporarily axially deflects the rotor 2.

Figure 2:
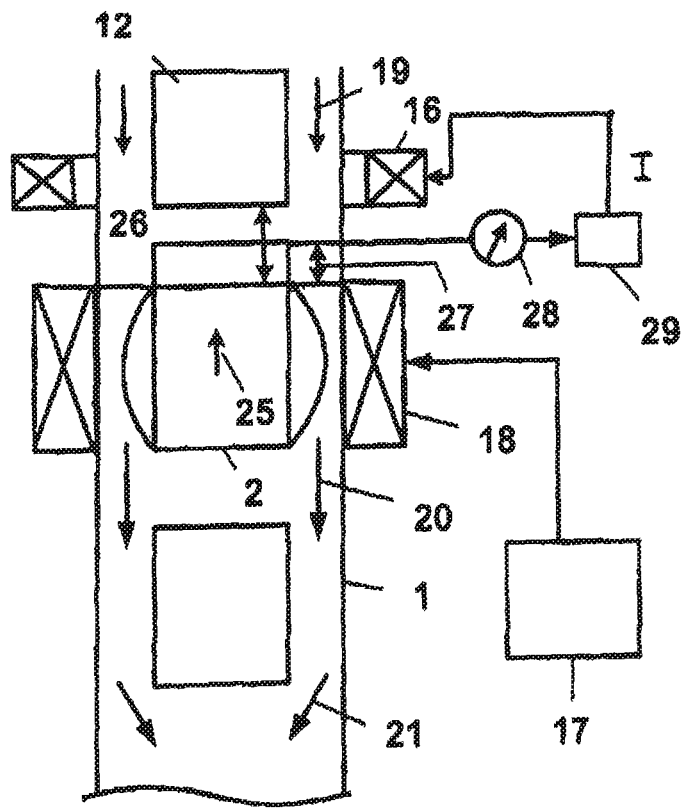
Figure 2:
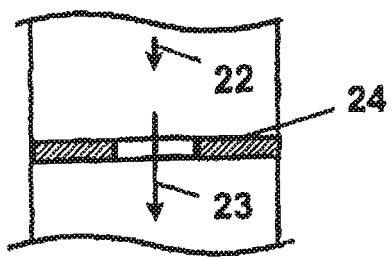

This procedure is described in more detail by way of FIG. 2, in which the elements already shown in FIG. 1, which are equivalent, are indicated with the same reference numerals.

The drive control is indicated in FIG. 2 at 17 and acts on a drive winding 18 which is shown only very schematically in FIG. 2 and which sets the rotor 2 into rotation. If it is the case of a synchronous motor as described, then one may already set a rotation speed with the drive control 17. Otherwise, one may additionally provide a rotation speed sensor in the region of the rotor 2, for measuring the rotational speed.

When the rotor 2 is set into rotation, the fluid flows through the tube 1 or its continuation, as is represented in FIG. 2 with the arrows 19, 20, 21, 22 and 23. The flow resistance parameters of the element 24 subjected to throughflow, in the form of an orifice, may be determined on operation by way of detecting the measurement variables in the region of the axial pump.

With the operation of the pump drive as is represented above, a force on the rotor 2 results, which is directed in the direction of the arrow 25 and seeks to reduce the axial gap to the stationary component 12. The size of this gap is indicated in FIG. 2 with the reference numeral 26, whilst the deviation from the desired position of the rotor, is indicated at 27. This deviation is detected by way of the sensor 28 which transmits this variable further to the control/regulation device 29 for the axial position of the rotor. This control/regulation device accordingly determines the necessary current i through the control coil 16 which influences the axial magnet field acting on at least one of the permanent magnets in the rotor 2.

In this manner, the axial position of the rotor is controlled with a closed loop and is held in the middle position in a stable manner.

The current strength i necessary for the control is a measure of the counter-force acting on the rotor 2, or the pump load, or also the pressure difference in the delivered fluid which is produced by the pump.

Figure 3:
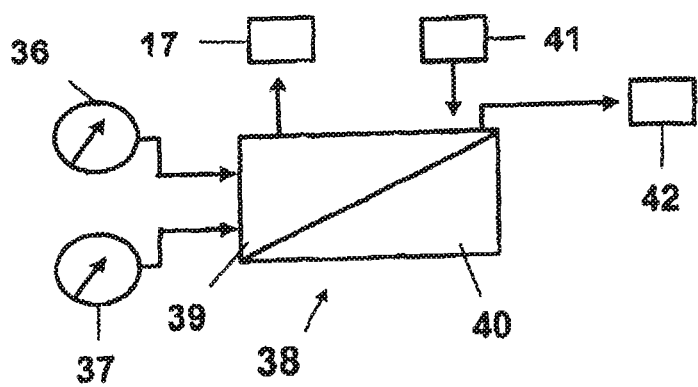

The structure of the measurement device and its application for measuring the flow path is to be represented hereinafter by way of FIG. 3.

Thereby, the sensor for the current strength, which is necessary for the thrust bearing stabilisation, is indicated at 36, and 37 indicate the sensors a rotational speed sensor of the rotor 2. The sensors are connected to the evaluation device 38 which comprises a comparison device 39 as well as a memory device 40. The respective characteristic fields for the rotational speed and current and position values are stored in the memory device 40. The evaluation device 38 furthermore activates the drive 17 of the rotor. Moreover, the evaluation device 39 may obtain information on the type or the viscosity of the applied fluid, via the input unit 41.

Subsequent to the comparison procedure, the evaluation device 38 transfers the evaluated flow resistance parameters to the output device 42.

The evaluation, instead of by way of comparison of measured values with the characteristic field, may also be effected by way of computation by way of an evaluation algorithm.

Hereinafter, it is to be described by way of FIG. 4, how a similar device may be used within the framework of a measurement of material characteristics. For this, FIG. 4 in a tube 1 schematically and in longitudinal section, shows a rotor 2 which is axially mounted in a magnetic manner by way of two annular permanent magnets 10, 10*a* which lie in the axial field of a stationary magnet device which is not represented in more detail and which produces an axial field, wherein the controllable magnet coils 16, 16*a* serve for axial stabilisation of the rotor 2 and may be activated by way of the closed-loop control device 29. The coils 16, 16*a* thereby produce an additional axial magnet field for positioning the rotor 2 in the axial direction.

Connected to the control device 29, is an excitation device 43 for oscillation excitation in the axial or radial direction, which for oscillation excitation in the axial direction for example activates one of the coils 16, 16*a*, or for oscillation excitation in the radial direction, activates an additional excitation coil 44 arranged on the outside on the tube 1.

An oscillation excitation or a one time excitation in the form of an impulse or a rectangular signal in the axial direction results in an axial oscillation of the rotor 2 in the axial direction which is indicated by the arrow 45, whilst a radial oscillation or one time excitation results in an oscillation in the radial direction indicated by the arrow 46.

The oscillation behaviour in the case of an axial oscillation on the one hand may be recorded by a sensor coil 47, in whose field region an immersed body 15 of the rotor acts. This sensor coil 47 may be independent or may also generally serve for bearing closed-loop control additionally to the position detection of the rotor 2, and in this case is connected to the closed-loop control device 29, and likewise to the measurement device for the detection of the oscillation behaviour.

In the case of a radial oscillation which may be initiated by the excitation coil 44, the radial position of the rotor 2 may be detected by way of an immersed body 48 and a sensor coil 49 at the outside on the tube 1 and likewise be led to the measurement device.

Figure 4:
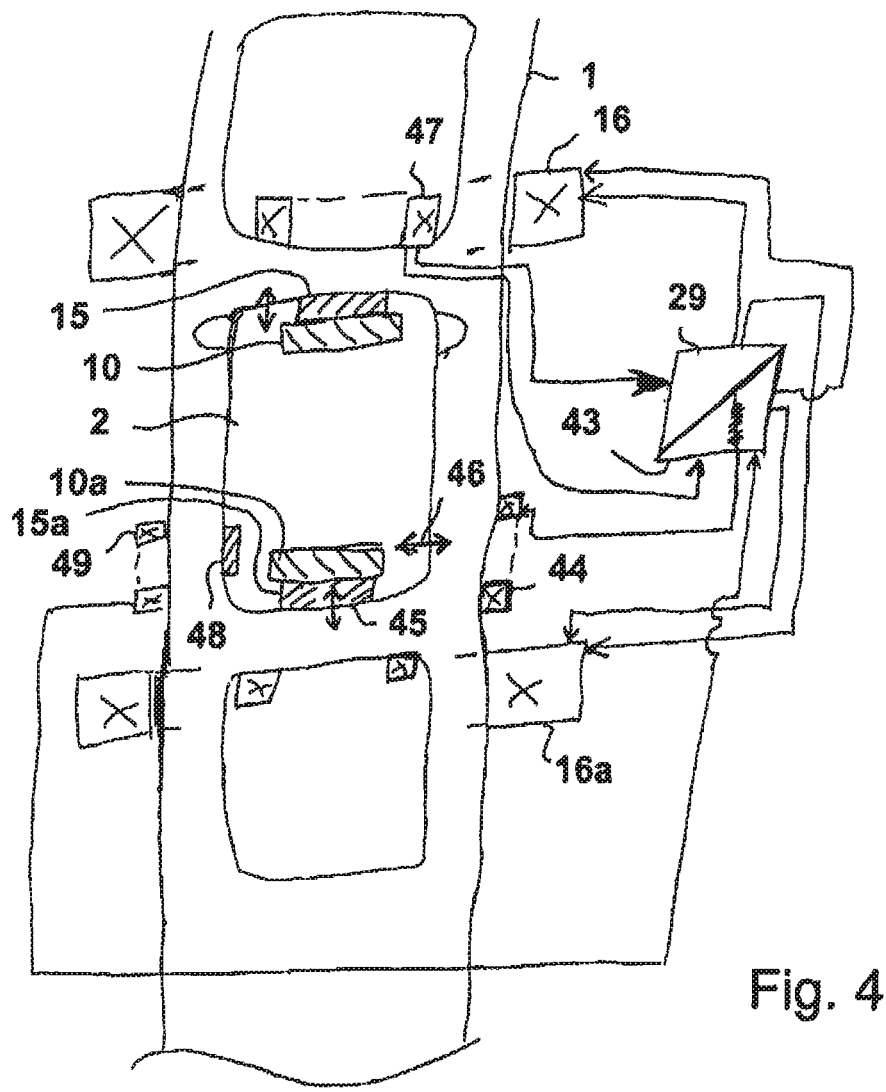

Alternatively to the axial excitation manner represented in FIG. 4, one may also envisage a separate magnetically effective coil which is different from the coil used for the bearing closed-loop control, being provided for applying an excitation signal.

Likewise, the sensor coil which is used for recording the oscillation behaviour, may be different from the sensor coil for the detection of the axial position of the rotor for the bearing closed-loop control.

On mustering a radial oscillation, the problem of the interaction with the bearing closed-loop control does not occur, as long as the magnet constellation of the stators located in the tube as well as of the rotor 2, is designed in a manner such that the magnet mounting is self-centring in the radial direction. This for example may be the case by way of the stators in each case carrying circular-disk-like magnets at their end-sides, which produce an axial magnetic field and which lie opposite the respective magnets 10, 10*a* in the rotor 2, which likewise are aligned axially with their magnetic field and are arranged concentrically to these. In this case, the bearing is radially self-centring, so that the rotor position, after applying a swing impulse in the radial direction, is centred on its own again after running through an oscillation with a suitable damping.

Figure 5:
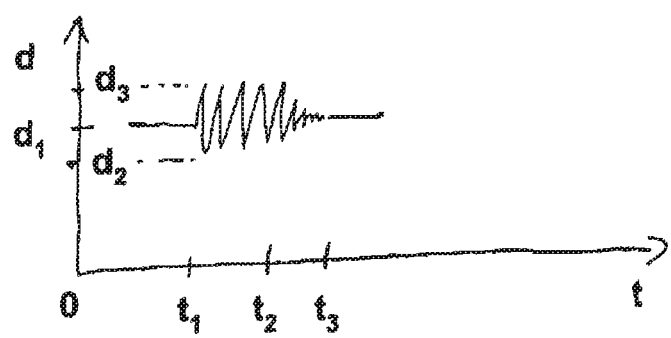

The typical oscillation behaviour is represented in the form of the amplitude plotted on the ordinate with respect to time, plotted on the abscissa, is shown in FIG. 5. The rotor assumes the position $d_1$ between the point in time 0 and $t_1$, and this position for example represents a stable condition between the rotor and a stator.

At the point in time $t_1$, a periodic swing, for example in the axial direction, is applied and is maintained as a forced oscillation for a time up to the point in time $t_2$. A certain amplitude of the oscillation $d_3$-$d_4$ results in dependence on the applied power.

The oscillation excitation is switched off at the point in time $t_2$ and the oscillation decays approximately exponentially (see logarithmic decay), whereas practically no or only a defined reduced swing may be ascertained at the point in time $t_3$. The time constant of the decay behaviour between $t_2$ and $t_3$, or for example the time between $t_2$ and the point of time, where the amplitude has been reduced to half the amplitude of $t_2$, may be measured, and describes the dissipation of the oscillation energy which, just as the amplitude, is dependent on the viscosity of the fluid surrounding the rotor. Otherwise, the rotor between $t_2$ and $t_3$ is located in an oscillation condition of the free oscillation, in which the frequency of the oscillation or the difference to the intrinsic frequency without damping or with a specific damping is dependent on the viscosity of the fluid surrounding the rotor and permits a deduction of the material parameters, for example the viscosity, of the fluid.

The described variables of the oscillation behaviour thus permit the evaluation of fluidic-effective parameters of the fluid, in particular of the liquid which surrounds the rotor.

Thus the invention, with the simplest of means, permits the use of a fluid pump which is often present in any case, for the measurement of fluidic characteristics of the delivered fluid, and as the case may be, in combination with this, likewise permits information on additional elements through which the fluid flows, by way of the measurement of the pressure drop in the pump and of the rotational speed.

The invention claimed is:

1. A blood pump system comprising:
   a blood pump, the blood pump further including a delivery element and a magnetic bearing, the magnetic bearing comprising a permanent magnet and a first coil;
   a closed-loop control device configured to stabilize the position of the delivery element; and
   an excitation device for the excitation of the delivery element against a counter-force applied by the magnetic bearing, the excitation device comprising a second coil,
   wherein the control device is further configured to determine at least one fluid-mechanically effective parameter of a fluid flowing by the delivery element.

2. The blood pump system according to claim 1, wherein the control device is coupled to a sensor for measuring an oscillation frequency of the delivery element.

3. The blood pump system according to claim 1, wherein the control device is coupled to a sensor for measuring an oscillation amplitude.

4. The blood pump system according to claim 1, wherein the control device is coupled to a time detection device for measuring an oscillation build-up behavior and/or an oscillation decay behavior of the delivery element.

5. The blood pump system according to claim 1, wherein the excitation device is connected to the closed-loop control device.

6. The blood pump system according to claim 1, wherein the magnetic bearing is an axial magnetic bearing.

7. The blood pump system according to claim 1, wherein the excitation device is configured for exciting the delivery element in an axial direction.

8. The blood pump system according to claim 1, wherein the excitation device is configured for exciting the delivery element in radial direction.

9. The blood pump system according to claim 1, wherein the control device is coupled to a sensor for measuring the excitation behaviour of the delivery element.

10. The blood pump system of claim 9, wherein the control device is configured to receive signals from the sensor in response to the excitation of the delivery element.

* * * * *